(12) United States Patent
Colacot et al.

(10) Patent No.: US 8,618,318 B2
(45) Date of Patent: Dec. 31, 2013

(54) PROCESS FOR THE PREPARATION OF PALLADIUM (I) TRI-TERT-BUTYLPHOSPHINE BROMIDE DIMER

(75) Inventors: Thomas John Colacot, Cherry Hill, NJ (US); Mark William Hooper, Oxford (GB); Gabriela Alexandra Grasa, Bowie, MD (US)

(73) Assignee: Johnson Matthey Public Limited Co., London (GB)

( * ) Notice: Subject to any disclaimer, the term of this patent is extended or adjusted under 35 U.S.C. 154(b) by 0 days.

(21) Appl. No.: 13/387,593

(22) PCT Filed: Jul. 27, 2010

(86) PCT No.: PCT/GB2010/051232
§ 371 (c)(1),
(2), (4) Date: Apr. 13, 2012

(87) PCT Pub. No.: WO2011/012889
PCT Pub. Date: Feb. 3, 2011

(65) Prior Publication Data
US 2012/0190873 A1 Jul. 26, 2012

Related U.S. Application Data

(60) Provisional application No. 61/229,982, filed on Jul. 30, 2009.

(51) Int. Cl.
*C07F 15/00* (2006.01)
(52) U.S. Cl.
USPC ............................................................ 556/23

(58) Field of Classification Search
USPC ............................................................ 556/23
See application file for complete search history.

(56) References Cited

PUBLICATIONS

Bercot et al., Organic Letters, vol. 10, No. 22, pp. 5251-5254 (2008).*
Vilar et al., "Synthesis and structural characterisation of [Pd$_2$(μ-Br)$_2$(PBu$^t_3$)$_2$], an example of a palladium(I)—palladium(I) dimer," *J. Chem. Soc., Dalton Trans.*, 1996, pp. 4313-4314.
Durà-Vilà et al., "Reactivity studies of [Pd$_2$(μ-X)$_2$(PBu$^t_3$)$_2$] (X=Br, I) with CNR (R=2,6-dimethylphenyl), H$_2$ and alkynes," *Journal of Organometallic Chemistry*, 2000, vol. 600, pp. 198-205.
Angurell et al., "About the different reactivity of dinuclear palladium and platinum compounds with trispyrrolylphosphine: Synthesis and X-ray crystallographic results of new palladium complexes containing P-pyrrolyl bonds," *Journal of Organometallic Chemistry*, 2007, vol. 692, pp. 3882-3891.
International Search Report dated Sep. 30, 2010, from PCT International Application No. PCT/GB2010/051232.

* cited by examiner

*Primary Examiner* — Porfirio Nazario Gonzalez
(74) *Attorney, Agent, or Firm* — RatnerPrestia

(57) ABSTRACT

The present invention provides a process for the preparation of a complex of formula (I) comprising the steps of: (a) mixing Pd(diolefin)Br$_2$ and $^t$Bu$_3$P in a solvent; and (b) adding an alkali hydroxide to form the complex of formula (I).

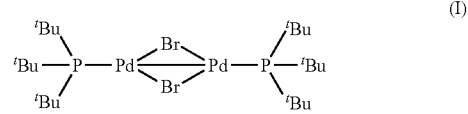

(I)

13 Claims, No Drawings

PROCESS FOR THE PREPARATION OF PALLADIUM (I) TRI-TERT-BUTYLPHOSPHINE BROMIDE DIMER

CROSS-REFERENCE TO RELATED APPLICATIONS

This application is the U.S. National Phase application of PCT International Application PCT/GB2010/051232, filed Jul. 27, 2010, and claims priority of U.S. Provisional Patent Application No. 61/229,982, filed Jul. 30, 2009, the disclosures of both of which are incorporated herein by reference in their entireties for all purposes.

FIELD OF THE INVENTION

The present invention concerns the preparation of precious metal complexes, in particular a palladium phosphine complex.

BACKGROUND OF THE INVENTION

Palladium(I) tri-tert-butylphosphine bromide dimer {[Pd (P$^t$Bu$_3$) (μ-Br)]$_2$} is an active catalyst for cross coupling reactions. Palladium(I) tri-tert-butylphosphine bromide dimer has been prepared by Mingos et al using either Pd$_2$dba$_3$.C$_6$H$_6$ or a combination of Pd$_2$dba$_3$.C$_6$H$_6$ and Pd(COD)Br$_2$ (J. Chem. Soc. Dalton Trans. (1996) 4313 and J. Organomet. Chem. 600 (2000) 198). Pd$_2$dba$_3$.C$_6$H$_6$ itself is prepared by crystallising Pd(dba)$_2$ in a large volume of C$_6$H$_6$. Pd$_2$dba$_3$.C$_6$H$_6$ is a highly air-sensitive catalyst which requires high vacuum and low temperature conditions for crystallisation.

SUMMARY OF THE INVENTION

It is an object of the present invention to provide an alternative process for the preparation of precious metal complexes, in particular palladium(I) tri-tert-butylphosphine bromide dimer.

Accordingly, the present invention provides a process for the preparation of a complex of formula (I):

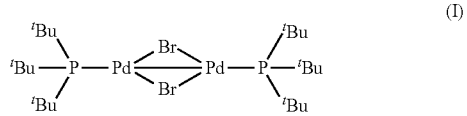
(I)

comprising the steps of:
(a) mixing Pd(diolefin)Br$_2$ and $^t$Bu$_3$P in a solvent; and
(b) adding an alkali hydroxide to form the complex of formula (I).

DETAILED DESCRIPTION OF THE INVENTION

The process of the present invention does not use Pd$_2$dba$_3$.C$_6$H$_6$ as a starting material. As such, the crystallisation of Pd(dba)$_2$ may be avoided. Furthermore, the preparation of [Pd (P$^t$Bu$_3$) (μ-Br)]$_2$ is facilitated as the complex does not become contaminated with dba ligand. The process of the present invention therefore is more suited to large-scale manufacture.

Preferably, the Pd(diolefin)Br$_2$ contains a cyclic diolefin, more preferably 2,5-norbornadiene (NBD) or 1,5-cyclooctadiene (COD). Suitable Pd(diolefin)Br$_2$ compounds therefore include Pd(COD)Br$_2$ and Pd(NBD)Br$_2$. Pd(COD)Br$_2$ is particularly preferred.

Alternatively, the diolefin can be replaced by two molecules of a monoolefin. In this instance, the monoolefin may be selected from the group consisting of a straight-chain C$_{2-10}$ alkene, a branched C$_{2-10}$ alkene, a C$_{5-10}$ cycloalkene and combinations thereof. More preferably, the monoolefin is ethylene or cyclooctene.

The Pd(diolefin)Br$_2$ compound and the $^t$Bu$_3$P ligand are mixed together in a solvent. The solvent may be selected from a group consisting of a straight chain, branched or cyclic C$_{1-10}$ alkanol, a C$_{6-10}$ aromatic hydrocarbon and combinations thereof. Preferably, the solvent is selected from the group consisting of methanol, ethanol, 2-propanol, 1-butanol, 2-butanol, 3-methyl-2-butanol, 2-methyl-2-butanol, 3-methyl-1-butanol, benzene, toluene and combinations thereof. Particularly preferred solvents are methanol and toluene. The concentration of Pd(diolefin)Br$_2$ in the solvent is preferably about 0.05 mol/L to about 2.5 mol/L and more preferably, about 0.2 mol/L to about 2 mol/L.

The $^t$Bu$_3$P ligand may be used as a solid or, more preferably, as a solution in a solvent such as toluene or tetrahydrofuran (THF). Any suitable concentration of $^t$Bu$_3$P in solvent may be used, although it is preferred that the molar ratio of Pd(diolefin)Br$_2$:$^t$Bu$_3$P is about 1:1. If desired, the molar quantity of $^t$Bu$_3$P may be in slight excess to the molar quantity of Pd(diolefin)Br$_2$. For example, the amount of $^t$Bu$_3$P in the reaction mixture may be calculated to provide a molar excess of up to about 10% over the amount required for the stoichiometric reaction.

In combining the Pd(diolefin)Br$_2$ and $^t$Bu$_3$P in the solvent, the components may be mixed in any suitable order, although preferably the Pd(diolefin)Br$_2$ is first added to the solvent, followed by $^t$Bu$_3$P.

In a particularly preferred embodiment of the invention, the solvents which may be utilised in step (a) may comprise at least a proportion of toluene. The present inventors have found that the inclusion of a suitable quantity of toluene results in the complex of formula (I) being obtained in a more crystalline form. In this respect, the solvent as described above for step (a) may comprise toluene, or the $^t$Bu$_3$P ligand may be added to the reaction mixture as a toluene solution.

After the Pd(diolefin)Br$_2$ compound and the $^t$Bu$_3$P ligand are mixed together in the solvent, preferably the reaction mixture is stirred at a temperature in the range of about −10° C. to about 35° C., preferably about −5° C. to about 30° C. The mixture may be stirred for a period e.g. preferably about 1 minute to about 3 hours, more preferably about 5 minutes to about 2 hours and most preferably about 10 minutes to about 1 hour.

An alkali hydroxide is added to the mixture of Pd(diolefin) Br$_2$ and $^t$Bu$_3$P. Preferably, the molar ratio of Pd(diolefin)Br$_2$: alkali hydroxide is about 1:1. If desired, the molar quantity of the alkali hydroxide may be in slight excess to the molar quantity of Pd(diolefin)Br$_2$. For example, the amount of alkali hydroxide in the reaction mixture may be calculated to provide a molar excess of up to about 10% over the amount required for the stoichiometric reaction.

The alkali hydroxide may be potassium hydroxide or sodium hydroxide, preferably sodium hydroxide. In one embodiment, the alkali hydroxide is added to the reaction mixture as a solid. Alternatively, the alkali hydroxide may be dissolved in a straight chain, branched or cyclic C$_{1-10}$ alkanol and then added to the reaction mixture as a solution. Suitable alkanols are methanol, ethanol, 2-propanol, 1-butanol, 2-butanol, 3-methyl-2-butanol, 2-methyl-2-butanol, 3-methyl-1- butanol or a combination thereof. Preferably, the alkanol is methanol. The alkali hydroxide/alkanol solution may be used in any suitable concentration, for example, in the range of about 0.05 mol/L to about 3 mol/L, preferably about 0.1 mol/L to about 2.5 mol/L.

After the addition of the alkali hydroxide, preferably the reaction mixture is stirred at a temperature in the range of about −10° C. to about 35° C., preferably about −5° C. to about 30° C. The mixture may be stirred for a period e.g. preferably about 1 minute to about 4 hours, more preferably about 5 minutes to about 3.5 hours and most preferably about 10 minutes to about 3 hours.

On completion of the reaction, the complex of formula (I) is separated from the reaction mixture by any appropriate method which is dependent on the physical form of the product. For example, when it is desired to recover the complex of formula (I) as a solid, the complex may be precipitated from the reaction mixture by the addition of a suitable solvent (e.g. methanol). The complex may then be isolated by filtering, decanting or centrifuging. The separated complex is preferably washed with further solvent and then dried. Drying may be performed using known methods, for example, at temperatures in the range of about 10-60° C. and preferably about 20-40° C. under about 1-30 mbar vacuum for about 1 hour to about 5 days.

It is preferred that all steps in the preparation and isolation of the complex of formula (I) are conducted under an inert atmosphere (e.g. nitrogen or argon). In addition, as the complex of formula (I) is not stable in water, it is preferred that the quantity of water which may be present in any of the solvents utilised is controlled. In one embodiment of the invention, therefore, the solvents are anhydrous.

The process of the present invention is high yielding and the catalyst obtained is pure. Accordingly, in another aspect, the present invention provides a complex of formula (I) obtainable according to the process as described above.

EXAMPLES

The invention will be further illustrated by reference to the following non-limiting Examples.

Example 1

After degassing three times under vacuum/$N_2$, Pd(COD)$Br_2$ (4.4 mol, 1.66 kg) in toluene suspension (2.3 L) was reacted with 1 mole equivalent $tBu_3P$ (4.5 mol, 909 g neat, 12% w/w in toluene) at room temperature for 30 min. The resulting solution was reacted with 1 mole equivalent of sodium hydroxide NaOH (4.6 mol, 185 g) solution in MeOH (2.2 L) at room temperature for 2 h. More methanol (19 L) was added to precipitate the product and the reaction mixture was stirred at room temperature for 1 h before being filtered and washed under inert conditions with methanol to give the product as a dark green solid. Total yield=90%. NMR and elemental assay indicate pure product as [Pd(t-$Bu_3P$)(μ-Br)]$_2$ (Pd(I)). Elemental: C=37.4 (37.0); H=7.13 (7.0); Br=20.95 (20.56)

Example 2

After degassing three times under vacuum/$N_2$, Pd(COD)$Br_2$ (133 mmol, 50 g) in toluene suspension (70 mL) was reacted with 1 mole equivalent $tBu_3P$ (135 mmol, 27.3 g neat, 12% w/w in toluene) at −5° C. for 15 min. The resulting solution was reacted with 1 mole equivalent of sodium hydroxide NaOH (135 mmol, 5.4 g) solution in MeOH (60 mL) at −5° C. for 30 min. More methanol (3.5 L) was added to precipitate the product and the reaction mixture was stirred at −5° C. for 1.5 h before being filtered and washed under inert conditions with methanol to give the product as a dark green solid. Total yield=85%. NMR and elemental assay indicate pure product as [Pd(t-$Bu_3$Pμ-Br)]$_2$ (Pd(I)). Elemental: C=37.03 (37.0); H=7.65 (7.0); Br=20.33 (20.56)

Example 3

A two-liter three necked flask was loaded with Pd(COD)$Br_2$ (133 mmol, 50 g) and was degassed three times under vacuum/$N_2$. To this was added 500 ml methanol using a cannula. To this was added t-$Bu_3P$ (135 mmol, 27 g) as a 10% THF solution by weight over a period of 15 minutes. A green colored reaction mixture resulted. After 10-15 minutes of stirring 5.4 g pure (99.9%) NaOH dissolved in 800 ml anhydrous, degassed MeOH was added using the cannula technique. Stirring was continued at RT for another 35 minutes. The dark green solid was filtered using a Schlenk frit under strict inert conditions. The product was washed thoroughly with 3×200 ml of anhydrous MeOH under nitrogen or until the washings are essentially colorless. Dried the solid under vacuum for about 6 hours, so as to obtain a free flowing powder (Yield: 45 g). Analysis: $^{31}$P NMR In $C_6D_6$: 87. 7 PPM; $^1$H NMR: Very close triplet at 1.45 PPM. Elemental: C=36.2 (37.0); H=6.88 (7.0); Br=20.00 (20.56)

The invention claimed is:
1. A process for the preparation of a complex of formula (I):

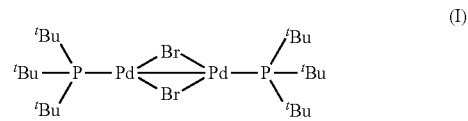

comprising the steps of:
(a) mixing Pd(diolefin)$Br_2$ and $^tBu_3P$ in a solvent; and
(b) adding an alkali hydroxide to form the complex of formula (I).
2. A process according to claim 1, wherein the diolefin is a cyclic diolefin.
3. A process according to claim 2, wherein the cyclic diolefin is 2,5-norbornadiene (NBD) or 1,5-cyclooctadiene (COD).
4. A process according to claim 1, wherein the diolefin comprises two molecules of a monoolefin.
5. A process according to claim 4, wherein the monoolefin is selected from the group consisting of a straight-chain $C_{2-10}$ alkene, a branched $C_{2-10}$ alkene, a $C_{5-10}$ cycloalkene and combinations thereof.
6. A process according to claim 4, wherein the monoolefin is ethylene or cyclooctene.
7. A process according to claim 1, wherein the solvent is selected from the group consisting of a straight-chain, branched or cyclic $C_{1-10}$ alkanol, a $C_{6-10}$ aromatic hydrocarbon and combinations thereof.
8. A process according to claim 1, wherein the solvent is selected from the group consisting of methanol, ethanol, 2-propanol, 1-butanol, 2-butanol, 3-methyl-2-butanol, 2-methyl-2-butanol, 3-methyl-1-butanol, benzene, toluene and combinations thereof.
9. A process according to claim 1, wherein the alkali hydroxide is potassium hydroxide or sodium hydroxide.

10. A process according to claim 1, wherein the concentration of Pd(diolefin)Br$_2$ in the solvent is about 0.05 mol/L to about 2.5 mol/L.

11. A process according to claim 1, wherein the molar ratio of Pd(diolefin)Br$_2$:$^t$Bu$_3$P is about 1:1.

12. A process according to claim 1, wherein the molar ratio of Pd(diolefin)Br$_2$:alkali hydroxide is about 1:1.

13. A process according to claim 1, wherein step (a) and step (b) are independently carried out at one or more temperatures between about −10° C. and about 35° C.

* * * * *

UNITED STATES PATENT AND TRADEMARK OFFICE
CERTIFICATE OF CORRECTION

PATENT NO.         : 8,618,318 B2
APPLICATION NO.    : 13/387593
DATED              : December 31, 2013
INVENTOR(S)        : Colacot et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 39 days.

Signed and Sealed this
Twenty-second Day of September, 2015

Michelle K. Lee
*Director of the United States Patent and Trademark Office*